United States Patent [19]
Meyer

[11] Patent Number: 4,624,673
[45] Date of Patent: Nov. 25, 1986

[54] DEVICE SYSTEM FOR DENTAL PROSTHESIS FIXATION TO BONE

[75] Inventor: Benjamin S. Meyer, Birmingham, Ala.

[73] Assignee: United States Medical Corporation, Washington, D.C.

[21] Appl. No.: 404,874

[22] Filed: Aug. 3, 1982

Related U.S. Application Data

[63] Continuation-in-part of Ser. No. 341,224, Jan. 21, 1982, abandoned.

[51] Int. Cl.$^4$ .............................................. A61F 2/28
[52] U.S. Cl. ...................................... 623/16; 433/173
[58] Field of Search ............... 433/173, 174, 172, 175, 433/171, 176; 3/1, 1.9; 128/92 C, 92 G

[56] References Cited

U.S. PATENT DOCUMENTS

| | | | |
|---|---|---|---|
| 2,210,424 | 8/1940 | Morrison | 128/92 C |
| 3,820,167 | 6/1974 | Sivash . | |
| 3,848,272 | 11/1974 | Noiles | 3/1.913 |
| 3,848,276 | 11/1974 | Martinez . | |
| 3,943,576 | 3/1976 | Sivash . | |
| 3,996,625 | 12/1976 | Sivash . | |
| 4,016,651 | 4/1977 | Kawahara et al. | 433/174 |
| 4,077,070 | 3/1978 | Sivash . | |
| 4,179,810 | 12/1979 | Kirsch | 433/176 |
| 4,219,893 | 9/1980 | Noiles . | |
| 4,293,302 | 10/1981 | Hassler et al. | 433/173 |
| 4,409,974 | 10/1983 | Freedland | 128/92 CA |

FOREIGN PATENT DOCUMENTS

| | | | |
|---|---|---|---|
| 0000549 | 2/1979 | European Pat. Off. | 623/18 |
| 0010527 | 4/1980 | European Pat. Off. | 3/1.912 |
| 0041591 | 2/1981 | European Pat. Off. | 3/1.912 |
| 2726297 | 12/1978 | Fed. Rep. of Germany | 3/1.913 |
| 2808740 | 7/1979 | Fed. Rep. of Germany | 623/23 |
| 2063680 | 6/1981 | United Kingdom | 433/174 |

*Primary Examiner*—Richard J. Apley
*Assistant Examiner*—David J. Isabella
*Attorney, Agent, or Firm*—Fleit, Jacobson, Cohn & Price

[57] ABSTRACT

A two part system for fastening a dental prosthesis to the jaw bone having as a first part, an externally threaded thin wall sleeve which resides entirely within the jaw bone. The threads or other surface features are confined to the area near the point where the prosthesis enters the jaw bone. The sleeve has integrally, or accommodates, a non-threaded stem which extends relatively deeply into the jaw bone. The inner bore of the sleeve is a cone of a mechanically self locking taper. The second part, which extends outwardly from the jaw bone through the gum tissue, has a mating external taper which is driven within the sleeve to be locked therein. The second part supports an artificial tooth, bridge or other dental appliance. The concept also is applicable to a prosthetic device for any body joint.

11 Claims, 8 Drawing Figures

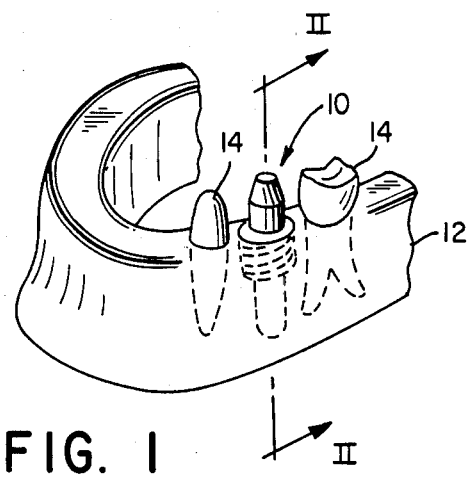
FIG. 1
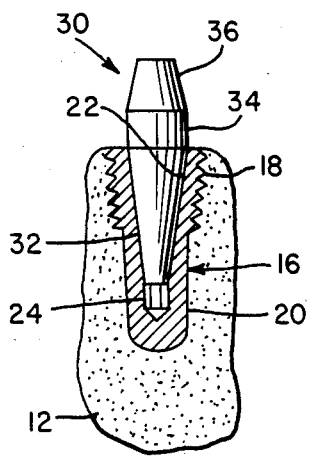
FIG. 2
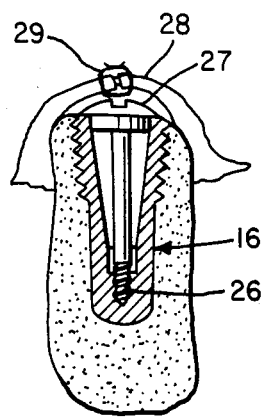
FIG. 3
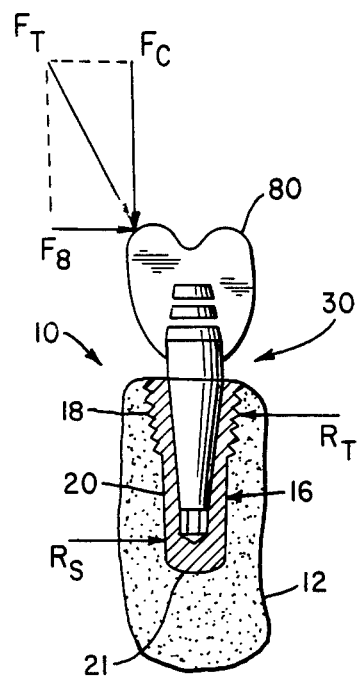
FIG. 7
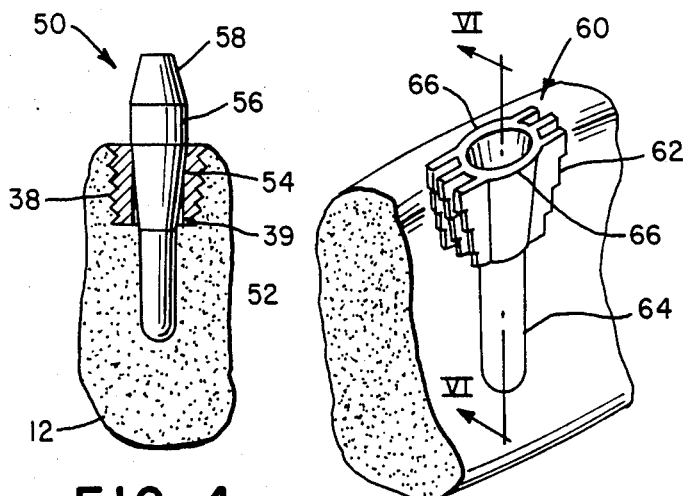
FIG. 4
FIG. 5
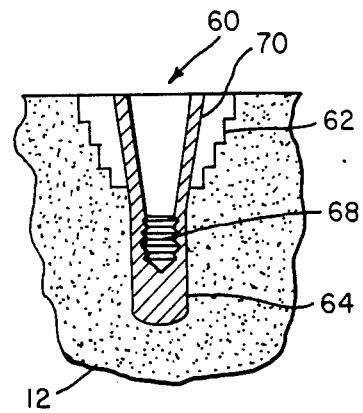
FIG. 6

DEVICE SYSTEM FOR DENTAL PROSTHESIS FIXATION TO BONE

This application is a continuation-in-part (CIP) of application Ser. No. 341,224 filed on Jan. 21, 1982, now abandoned.

BACKGROUND OF THE INVENTION

Field of the Invention

For more than ten years, attempts to implant devices in human jaw bones where natural teeth are missing have not been successful to the point where even one moderately well accepted design exists. Experience to date has demonstrated that remodeling of the jaw bone to accommodate the nonphysiological stress patterns introduced by the artificial implant generally causes an undesired reduction in the total volume of bone. It is a principal of physiology that bone develops shape and density according to the manner in which load is imposed on it. A change of shape or density on account of a change of loading is called bone remodeling. Further, the loss of bone is generally in that part of the jaw where the implant emerges from the bone to support the artificial tooth, bridge or other dental appliance. This loss of bone is at least partly attributed to the reduced stress in that part of the bone where the implant emerges from the bone. This occurrence has been reported particularly in patients fitted with blade type implants.

Functional loads imparted to a natural tooth or an implant are principally compression and bending. There is little likelihood of any significant torsion load being present. Current practice in implanting dental anchorage devices favors non-loading of the implant for an initial period of 2 to 4 months during which time the bone supporting the implant recovers from the trauma of the implantation procedure. This has been conveniently accomplished by using a two or more part device, where the bone anchorage part is implanted wholely within the jaw bone and the gum tissue is closed over the implant for the initial time period. One surface of the implant is approximately flush with the alveolar ridge of the mandible or maxilla and through this surface there has been provided a female thread, into which a second part of the prosthesis having a threaded male stem can be fastened when the gum tissue is penetrated for so doing.

The above known implanted parts may be externally smooth or threaded posts or cylinders, or blades. Any of which may be of metal, carbon, plastic or ceramic, either solid or porous, and uncoated or coated with a variety of biologically acceptable materials.

To our knowledge all of the above are designed for approximately equal or uniform bony attachment to all imbedded surfaces, and certainly in no instance is there provision for enhanced bony fixation in the area near the alveolar ridge and for less enhanced bony attachment to that part of the implant which extends relatively more deeply into the jaw bone, either mandible or maxilla.

Accordingly, a primary object of the present invention is to provide a dental prosthesis for implantation in the jaw bone by which compression load to the prosthesis is transferred primarily to the bone area adjacent to the alveolar ridge in order to maintain and develop sound bone in this critical area by stress remodeling of the bone; while at the same time transferring to the bone, lateral compressive stress reactions to bending loads applied to the implant, (1) as lateral compressive stress at the area adjacent the alveolar ridge and, (2) as lateral compressive stress at an area displaced from the alveolar ridge wherein the above opposed lateral compressive stresses are within the physiological stress capacity of the jaw bone.

An additional object is to provide a dental implant where that part implanted within the jaw bone immediately adjacent the alveolar ridge has its external bone interface surface area increased by geometric features or surface texture and that part implanted distant from the alveolar ridge lacks features which would increase its surface area.

An additional object is to provide the part of a dental implant prostheseis which passes through the gum to be of high endurance strength by making this part to be without external surface discontinuities such as those created by the presently used screw threads.

An additional object is to provide a dental implant prosthesis which has immediate structural intimate relationship with the jaw bone in order to prevent motion between the prosthesis and the bone.

An additional object is to provide a system where the part of the dental implant which passes through the gum can be firmly anchored in any radial angular position. That is, security of fastening is not a function of rotary thread tightening or other limitation.

An additional object is to provide the above advantages while at the same time also providing a two part dental prosthesis which permits an initial implantation of only one part, which part lies flush within, or below, the alveolar ridge of the jaw bone, so that the gum may be closed for a time of healing of the bone, after which the second part which passes through the gum issue may be installed.

SUMMARY OF THE INVENTION

To achieve these and other objects, the present invention provides a two part support for a dental prosthesis, one part of which is implanted entirely within the jaw bone. Of the implanted part, that portion adjacent the alveolar ridge has its external bone interface contact surface area significantly increased by screw threads, and that portion distant from the alveolar ridge lacks the external thread which increases the bone interface contact surface area of the adjacent portion. The other part, which projects outward from the crest of the jaw bone through the gum tissue, fits within the first part and is held therein by a self-locking mechanical taper.

In the preferred two part embodiment, the part implanted in bone is an elongated hollow tubular member closed at one end. The outer surface of the closed end is smooth and the outer surface of the open end is threaded in the manner of a self-tapping bone screw. The self-tapping thread is preferred because bone chips created during insertion stay in contact with the threads to fill spaces, which exist due to the porous nature of bone, to become nuclei for the growth of new bone in the manner of a bone graft. The thread may be tapered or straight. The opening in the threaded end of the member provides the female cone of a self-locking taper.

The part which extends outward from the bone, through the gum tissue to support the prosthesis is a pin, stud, or post having three zones. One end of this part is a zone which is the male cone of a self-locking taper which fits within the implanted hollow tubular member. The center zone of this part is a smooth cylinder which extends through the gum tissue. The other end of this part is a zone on which is mounted the prosthetic appliance, bridge or single tooth by any suitable means, as for instance by a second self-locking taper. A single tooth may be fused directly to this other end.

A second embodiment provides a threaded sleeve with a self-locking taper therethrough and a prosthesis supporting post which extends through the sleeve and into direct contact with the bone. The length of the post in contact with the bone has a smooth surface and is at least as long as the threaded sleeve.

A third embodiment provides increased interface contact area with bone by means of multiple longitudinal fins or flutes rather than screw threads. The fins or flutes are preferably self broaching.

For implantation of each of the above embodiments, the jaw bone is prepared by drilling and reaming a hole in the jaw bone accurately sized to receive the smooth end of the implant in a tight fit and is also sized to accept the root diameter of the threaded or fluted end of the implant. Thus, the threads or flutes must cut their way into the bone. This action provides immediate intimate structural relationship between the prosthesis and the bone, thereby preventing motion between the prosthesis and the bone during the post operative period. It has been shown that motion between the prosthesis and the bone will cause the development of soft non-bony tissue which is inadequate to support the prosthesis.

The implanted material must be biologically acceptable to the development of bone in intimate contact with the prosthesis. Preferably the inventive prosthesis parts are made of titanium or titanium alloy, especially an alloy known as Ti6 Al 4V. These metals are highly resistant to corrosion and are well tolerated by the body. Their strength and stiffness characteristics are appropriate to this use, as is well known.

BRIEF DESCRIPTION OF THE DRAWINGS

FIG. 1 is a perspective view of part of a lower jaw bone showing an implant embodying the teachings of the present invention;

FIG. 2 is a sectional view through the implant and jaw bone in the plane indicated in FIG. 1;

FIG. 3 is a sectional view in the same plane as FIG. 2, showing a temporary screw plug in place in the tubular member;

FIG. 4 is a sectional view through the jaw bone and an implant of an alternate embodiment;

FIG. 5 is a fragmentary perspective view of a lower jaw bone showing another alternate embodiment;

FIG. 6 is a section through the implant of FIG. 5 in the plane indicated in FIG. 5;

FIG. 7 is a sectional view similar to FIG. 2 showing the reaction forces applied to the implant by the jaw bone due to a bending force component applied to a prosthetic tooth; and FIG. 8 is a sectional view through the bone and an additional embodiment of the implant according to the present invention.

DESCRIPTION OF THE PREFERRED EMBODIMENTS

With reference now to the drawings, wherein like reference characters designate like or corresponding parts throughout the several views, there is shown in FIG. 1 the two part support for a dental prosthesis 10 implanted in jaw bone 12 between two natural teeth 14. The drawings, except where noted, omit showing the soft gum or gingival tissues.

FIG. 2 shows, in section, the hollow tubular member 16 which has external thread 18 and one end, the closed end 20 with a smooth exterior and the self locking internal taper 22. Thread 18 and the smooth exterior of closed end 20 each occupy about half the length of hollow tubular member 16. Member 16 also has a hexagonal or splined socket at 24 with which a suitable inserting tool engages for screwing member 16 into the prepared cavity in jaw bone 12.

The prepared cavity in jaw bone 12 accepts member 16 so that the smooth closed end 20 is a tight fit. That is, the diameter of the reamed hole is somewhat smaller than the diameter of smooth portion 20. The nature of the bone within jaw bone 12 yields to accept portion 20 in the manner in which a piece of wood accepts a nail driven into an undersized pilot hole. The prepared bone cavity is reamed to approximately the root diameter of screw thread 18 of member 16 to the depth that the screw thread 18 penetrates the jaw bone. The hole in the jaw bone may be tapped prior to implanting member 16, but preferably thread 18 is of self tapping design. When such a self tapping thread is inserted once and left in position, the bone chips created during the insertion lie in the interface between the threads and the bone, filling small spaces which exist in the bone, and serve as nuclei for the growth of new bone cells which more firmly anchor the implant.

FIG. 2 shows the second member, pin 30, positioned within tubular member 16. Pin 30 has three zones, each with a different function. The zone at 32 is a male self locking taper which mates with the corresponding female self locking taper 22 within member 16. The central zone 34 is generally cylindrical and smooth and is that portion which passes through the gum tissue which covers jaw bone 12. The third zone 36 serves as the fastening are for the prosthetic bridge, tooth, or appliance. The zone 36 is shown as a male self locking taper, but could have any suitable configuration such as a male or female screw thread, or a grooved configuration as shown in FIG. 7 where a single artificial tooth is fused or cemented directly to pin 30.

The structure of FIG. 1 can be created at the time of implantation and the pin 30 used for limited function while the bone and gum tissue heal around the implant because the implanted system has sufficient mechanical strength to prevent unwanted motion between the implant and the bone. However, some practitioners currently favor a more conservative postoperative course using the means shown in FIG. 3.

In FIG. 3, tubular member 16 is provided with a female screw thread 26 formed in a recess at end of socket 24 in the closed end. A temporary screw plug 27 is inserted to seal the opening in tubular member 16, after which gum tissue 28 is closed over the implant by suture 29. This condition is maintained for the desired time, perhaps 2 to 4 months, during which time the bone and gum tissue recover from the trauma of surgery and the bony anchorage of member 16 becomes even more secure. After this time of healing, the gum tissue is opened, plug 27 removed and pin 30 is securely inserted.

When the implant is functional, loads are transmitted to the bone by the implant in a manner different from that done by the natural tooth. Therefore, the jaw bone will remodel its shape and density to accommodate the new load distribution pattern. The desirable load transmission pattern of the invention will be discussed with reference to FIG. 7. The total load on the artificial tooth 80 and the implant 10 is shown as $F_T$. The largest component of $F_T$ is known to be downward compression force $F_C$. Compression force $F_C$ is transmitted from the implant 10 to the bone 12 by shear and bending of the bone adjacent screw threads 18, by shear at the interface between the bone and smooth surface 20, and by compression of the bone beneath closed end 21. The greatest area of contact between implant 10 and bone 12 is at screw thread 18. Therefore, the greatest amount of load will be transmitted to the bone at the screw thread. This load transfer will cause an increase in the amount and density of bone adjacent the screw threads. This occurrence is most desirable because recession of bone at this alveolar ridge area has been an ever present problem inhibiting long term success in most dental implants to date. Design proportions and post-operative activity must be controlled to keep the stress on the bone within physiological limits, because excessive stress is also reported to cause destruction of bone. However, with generous surface area of the threads and gradually increasing functional loads, the jaw bone will remodel itself to support the prosthesis in a favorable manner.

The benefit of increased implant to bone interface area adjacent the alveolar ridge is vividly illustrated with respect to the bending load component $F_B$ applied to the artificial tooth 80. Bending component force $F_B$ will cause two reactive bending forces to occur between the bone and the implant, shown at $R_T$ operating on the threaded area 18 of implant 10 and $R_S$ operating on the smooth closed end portion 20 of implant 10. Depending on geometry, $R_S$ may be approximately equal to $F_B$. Force $R_T$ must equal $F_B$ plus $R_S$, because the summation of horizontal forces must be equal to zero. From this we see that $R_T$ must be approximately equal to twice $R_S$. Accordingly, the interface between implant and bone should be larger at $R_T$ that it is at $R_S$. The inventive construction satisfies this requirement.

An alternate embodiment is shown in FIG. 4, comprising a tapered external threaded sleeve 38 into which is received pin 50. The four functional zones of pin 50 are the smooth extended end portion 52 which fits securely in a prepared cavity in bone 12, the self locking male taper 54 which fits within sleeve 38, the generally smooth cylinder 56 which penetrates the gum tissue, and the bridge, tooth or appliance mounting portion 58, which is again shown as a male self locking taper. This embodiment has the advantage that several external size variations of sleeves 38 can be combined with several length variations of pins 50 to provide a greater number of overall size combinations with fewer parts than can the construction of FIG. 2. This makes for more economy in manufacturing and in sales and hospital inventory storage. To provide for closed early healing, a temporary stub pin having only zones 52 and 54 can be implanted during the time the gum tissue remains closed over the implant. Alternatively, only sleeve 38 can be implanted initially with a temporary plug of zone 54 shape in place while the implant is covered. In this case, the cavity for zone 52 of pin 50 would be prepared after the time of initial bone healing around sleeve 38. Sleeve 38 can be made with fluted or hex splines 39 in the small end of its bore to provide means for driving into place, and for removal if necessary.

A second alternative embodiment of the tubular member is shown as member 60 is shown in FIGS. 5 and 6. The principle of increased bone to implant interface area adjacent to the alveolar ridge is provided by the multiple longitudinal fins 62. This embodiment permits a somewhat larger pin to be used because the walls of tubular member 60 can be thinner at the buccal and lingual regions 66 due to the absence of external threads. In this case, the compression load component $F_C$ is transmitted to the bone adjoining fins 62 more by shear than by compression or bending, and providing a porous or textured surface on the fins is advantageous. The prepared bony cavity for this implant is sized to accept the tapered portion 70 and the extended portion 64 with a secure tight fit, as described above, and the fins are preferably shaped to broach or cut their own path into the bone 12. Again bone chips created by the broaching act as nuclei for new bone growth. Thread 68 is provided for attachment of an inserting tool for use during the implant procedure. It permits removal of one size of tubular member 60 when the clinician believes that use of a larger size would be desirable.

Smooth cylinder 20 (FIG. 2), smooth cylinder 52 (FIG. 4) or smooth cylinder 64 (FIG. 5) may be substituted by a cruciform shape 74 (four flutes), such as shown in FIG. 8, or any irregular or other regular cross section (including a varying cross section). The important feature is that the surface area of the upper half of member 16 (FIG. 2), and its corresponding part in the other figures, is at least twice the surface area as the lower half.

Numerous modifications and variations of the present invention are possible in the light of the above teachings. For instance, certain porous coatings could be applied to the implanted surface adjacent the alveolar ridge, while the deeper implanted surface could be uncoated and smooth. Or the closed end of the pin may have a cruciform cross section to increase its flexibility and thereby perhaps improved the force transfer pattern between prosthesis and bone. Also the outer surface of the implant as illustrated may be a porous metal, ceramic, plastic or carbon or may be treated with a biologically active coating. The invention is applicable for other implants in the human or animal skeleton, as for instance for artificial joints. It is therefore understood that within the scope of the appended claims, the invention may be practiced otherwise than as specifically described.

What is claimed is:

1. A component for use in a prosthetic joint comprising a hollow tubular means which has a closed end and an open end, the portion of said tubular means which is adjacent the open end having external features which increase its surface area to at least twice the surface area of the portion adjacent the closed end and the inner surface of said portion adjacent the open end defining a female part of self-locking taper; and elongated pin means having a first section which is adjacent to one end of said pin means defining a male cone of self-locking taper which is received in said female part and coacts therewith and a second section which is adjacent the other end of said pin means which projects from the open end of said hollow tubular means to serve as a support for a joint motion surface.

2. A component as defined in claim 1 wherein said external features are a self tapping thread.

3. A component as defined in claim 1 wherein said external features are flutes which broach the bone upon implantation without the aid of additional reaming.

4. A component as defined in claim 1 wherein the portion adjacent the closed end is a smooth cylinder.

5. A component as defined in claim 1 wherein the portion adjacent the closed end is cruciform in cross section.

6. A component as defined in claim 1 wherein the portion adjacent the closed end is tapered.

7. A component as defined in claim 1, wherein the external surface of the portion adjacent the open end is defined by self-tapping thread means.

8. A component as defined in claim 1, wherein the external surface of the portion adjacent the closed end is defined by a cylinder.

9. A component as defined in claim 1, wherein the cylinder is smooth.

10. A component as defined in claim 1, wherein the external surface of the portion adjacent the closed end is defined by a geometry of uniform cross section.

11. A component as defined in claim 10, wherein the geometry defines a cruciform.

* * * * *

UNITED STATES PATENT AND TRADEMARK OFFICE
CERTIFICATE OF CORRECTION

PATENT NO. : 4,624,673

DATED : November 25, 1986

INVENTOR(S) : Benjamin S. Meyer

It is certified that error appears in the above-identified patent and that said Letters Patent is hereby corrected as shown below:

In the drawings, Sheet 1, Fig. 3, the reference numeral 24 and lead line should be applied to the socket at the closed end of the tubular member 16 as illustrated below:

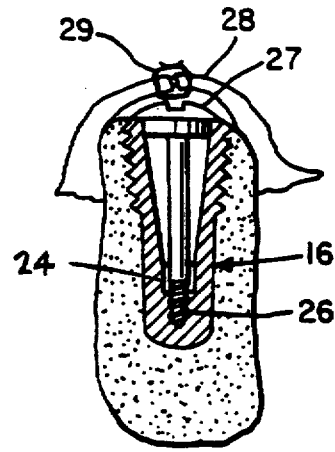

FIG. 3

Signed and Sealed this

Twenty-fourth Day of December, 1996

Attest:

BRUCE LEHMAN

Attesting Officer     Commissioner of Patents and Trademarks